United States Patent [19]

Strohschein

[11] Patent Number: 4,511,435
[45] Date of Patent: Apr. 16, 1985

[54] NON-FLOODING DISTILLING COLUMN

[76] Inventor: Rudy Strohschein, Rte. 1, Box 83, Micanopy, Fla. 32667

[21] Appl. No.: 344,684

[22] Filed: Feb. 1, 1982

[51] Int. Cl.$^3$ .............................................. B01D 53/20
[52] U.S. Cl. ............................. 202/158; 203/DIG. 2; 261/62; 261/114 VT
[58] Field of Search ........................ 202/158, 159, 153; 203/DIG. 2, DIG. 22; 261/62, 114 VT, 113 R; 422/193; 196/100, 139; 65/108

[56] References Cited

U.S. PATENT DOCUMENTS

| | | | |
|---|---|---|---|
| 3,293,149 | 10/1966 | Lengemann et al. | 261/114 VT |
| 3,325,155 | 6/1967 | Bahout | 261/114 VT |
| 3,493,218 | 2/1970 | Castellucci | 261/DIG. 72 |
| 3,607,661 | 9/1971 | Cerny et al. | 203/DIG. 2 |
| 3,759,494 | 9/1973 | Axelrod et al. | 261/114 VT |
| 4,098,579 | 7/1978 | Starzycki et al. | 261/114 VT |
| 4,136,976 | 1/1979 | Leffelman | 261/DIG. 72 |
| 4,201,626 | 5/1980 | Asdigian | 261/114 VT |

FOREIGN PATENT DOCUMENTS 38-2973  4/1963  Japan .................... 261/114 VT

OTHER PUBLICATIONS

Carney, T. P.: *Laboratory Fractional Distillation* N.Y. 1949, pp. 58–63.

Primary Examiner—Wilbur L. Bascomb, Jr.
Attorney, Agent, or Firm—Duckworth, Allen, Dyer & Pettis

[57] ABSTRACT

A Snyder-type distilling column having improved floating ball vapor valves. When used in a standard Snyder-type column, the valve comprises a spherical upper portion and a downwardly extending guide stem. When used in a microcolumn, the upper portion is mushroom shaped with a downwardly extending guide stem. The lower surface of either upper portion forms the valve face and includes multiple indentations therein. When a ball valve is closed, the indentations form by-pass passages to permit draining of condensed liquids therethrough thereby preventing flooding of the column. The indentations also permit the passage of vapors through the ball valve indentations thereby preventing sticking which can occur with a tight fitting ball valve and cause rotation of the ball valve during use which also assists in preventing sticking.

5 Claims, 6 Drawing Figures

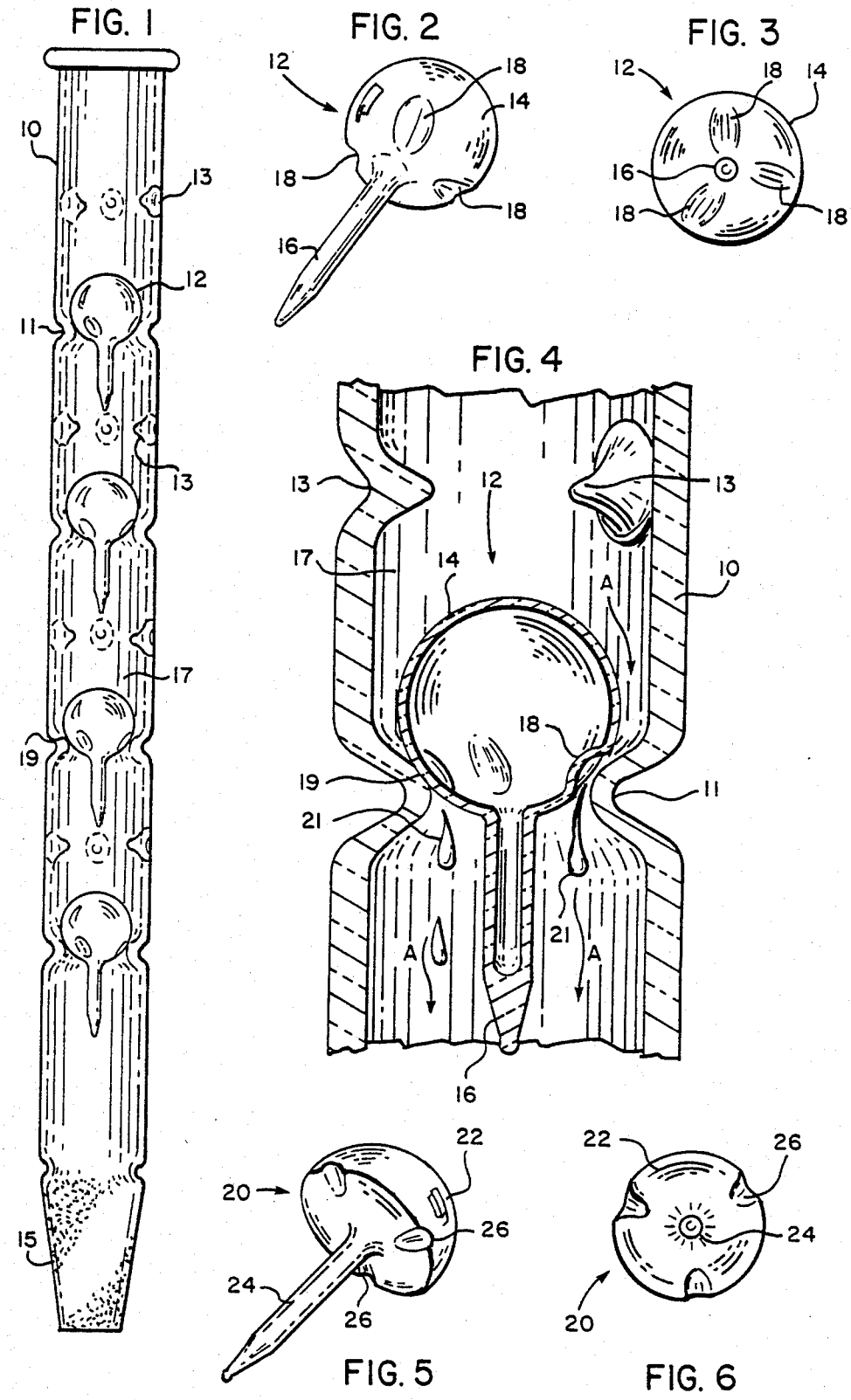

NON-FLOODING DISTILLING COLUMN

BACKGROUND OF THE INVENTION

1. Field of the Invention

The present invention relates to laboratory distilling columns and more particularly to a floating ball vapor valve type Snyder column which is free from flooding.

2. Description of the Prior Art

It is often necessary to separate mixtures from one another by distillation in various laboratory techniques. Distilling columns are commonly used for this purpose. In the conventional Snyder column, a vertical glass column is provided having a plurality of indentations around the circumference of the column forming a series of chambers joined by orifices. A hollow glass ball with a downwardly directed stem is disposed inside of the column at each indentation point with each orifice forming a valve seat. As the vapors of the various weight volatiles pass upward through the column, the ball vapor valves will lift allowing the vapors to pass from chamber to chamber. As the heavier fractions condense out, the resulting liquid will flow downward as the ball valves open. This process is known as fractional distillation and is widely used in the Kuderna-Danish technique as a concentration method for pesticide analysis.

One of the disadvantages of the prior art Snyder columns is a tendency for the balls to stick due to the tight fit of the valve in the orifice. When this occurs the condensing liquid from above will be trapped in the chamber, resulting in flooding. When a prior art valve sticks due to a tight fit in its seat, continuing vapor pressure buildup below may eventually result in a breaking loose of the ball, surging and sputtering of the trapped liquids and possible breakage of the apparatus.

The flooding phenomena is peculiar to Synder columns as well as to a number of types of vertical cylindrical reactors having bubble plate columns. A variety of special designs of the floating ball vapor valves has been tried; for example, in U.S. Pat. No. 4,098,579 to Starzycki, et al, spherical, mushroom shaped, hemispherical, cone shaped, and plate shaped valves are described. However, none of these are effective in preventing flooding due to sticking of the valve in its seat.

SUMMARY OF THE INVENTION

The present invention overcomes the flooding problems of the Snyder-type columns and prior art ball valves by a novel improvement in the floating ball vapor valve. The invention is applicable to any type of distilling bubble column and is particularly suitable for the Snyder column. The implementation of the invention in a Snyder column contemplates a vertical glass column formed from glass tubing having several chambers in tandem defined by a 360° circumferential indentation at the lower end of the chamber. Each chamber includes a hollow glass ball lift valve which, in one implementation, is spherical having a vertically oriented closed stem projecting downward with the ball resting on the inner walls of the indentations with the indentation thereby representing a seat for the ball valve. However, the ball portion of the ball valve does not completely seal the valve seat as in prior art columns by virtue of several indentations in the seating area of the ball. These indentations provide a small passage area from an upper chamber to the next lower chamber, even when the ball valve is in its closed position.

The hollow ball valve will float from the rising vapors when the column is in use, as with the prior art Snyder columns. However, the passage is not completely blocked when the ball valve is in the closed portion and any build up of liquids above the ball will quickly drain via the passages formed from the indentations in the ball. Thus, flooding of the chamber above a closed valve is avoided. Also, since the valve is not tight fitting as in the prior art there is no vapor pressure buildup to release a tight fitting valve with a resultant sudden surge of the vapor and liquids within the chamber, sputtering of liquid, or possible breakage.

It has been found that with continuing operation of the system, the fresh vapor and the continuing flow of the heavier condensed fractions will generally result in a moderate vibration of the ball valve maintaining it free from any tendency to stick.

As may now be recognized, a process once started can be continued and the normal loss of time and inefficiency resulting from having to halt the process to clean the column when sticking occurs is eliminated. It has also been found that breakage is greatly reduced and valve sticking is relatively uncommon. Preferably, the indentations are non-uniform resulting in the valves having greater movement than prior art ball valves which is effective in preventing sticking. Greater bubble pattern control through the use of the invention reduces sputtering and surging.

The spherical shaped valve is particularly well suited to standard Snyder column use. However, in accordance with the invention, the ball valve is not necessarily spherical shaped and other shapes may be used. For example, it has been found that a microcolumn may best utilize a mushroom shaped ball having the novel indentations in its seating area.

Therefore, it is a principle object of the invention to provide a distillation column having floating ball vapor valves with indentations in the seat areas thereof to prevent flooding during use.

It is another object of the invention to provide a Snyder column with floating ball vapor valves having indentations which assure optimum vapor/liquid contact without column flooding.

It is still another object of the invention to provide a ball valve for a Snyder column having an essentially spherical portion and a vertical stem portion in which the seating area of the spherical portion includes indentations.

It is yet another object of the invention to provide a floating ball vapor valve having a mushroom shape in which the underside of the mushroom shape serves as a valve seat and includes indentations therein.

It is a further object of the invention to provide a glass Snyder-type distillation column having a multiplicity of chambers having a valve seat between adjacent chambers for accepting the above described floating ball vapor valves in which valve sticking is prevented, column flooding is prevented, and breakage is reduced.

It is still a further object of the invention to provide a macro type glass distillation type column having the above described advantages in which the floating ball vapor valve is spherical and has a downward projecting closed stem.

It is yet a further object of the invention to provide a micro type glass distillation column having the advantages described above in which the floating ball vapor valve is mushroom shaped.

These and other objects and advantages of the invention will become apparent from the following detailed description when read in conjunction with the drawings.

DETAILED DESCRIPTION OF THE DRAWINGS

FIG. 1 is a Snyder-type distillation column in accordance with the invention utilizing spherical floating ball vapor valves;

FIG. 2 is a perspective view of a floating ball vapor valve of FIG. 1;

FIG. 3 is a bottom view of the valve of FIG. 2;

FIG. 4 is a partial cross sectional view of the column of FIG. 1 indicating the action of the ball valve when in the closed position;

FIG. 5 is a perspective view of another design shape of a floating ball vapor valve particularly suitable for microcolumns; and FIG. 6 is a bottom view of the micro valve of FIG. 5.

DETAILED DESCRIPTION OF THE PREFERRED EMBODIMENT

The present invention includes a novel floating ball vapor valve design for use in distillation columns and is particularly well suited for application to the Kuderna-Danish concentrator utilizing a Snyder column. For that reason, a Snyder column will be disclosed as the preferred embodiment for describing and explaining the invention. However, it is to be understood that the novel valve construction may be utilized in any type of distillation column including bubble plate types.

Turning to FIG. 1, a typical column is shown having a glass column 10 divided into a multiplicity of chambers 17 by 360° indentations 11. Each indentation provides an interior valve seat 19.

In the column of FIG. 1, four valve seats 19 are provided having four floating ball vapor lift valves 12 disposed thereon. As best seen in FIGS. 2, 3 and 4, ball valve 12 is formed by a hollow glass ball or sphere 14 having a stem portion 16 which is closed off to seal sphere 14. Sphere 14 rests on the inner valve seats 19 to essentially close off chambers 17 from each other. Indentations 13 in the wall of column 10 are provided to encapture ball valve 12 so as to prevent vapors during distillation from dislodging valve 12 completely.

In accordance with the invention, the area of sphere 14 that is in contact with valve seats 19 has several indentations 18 pressed into the seat area. For example, ball valve 12, illustrated in FIGS. 2 and 3, has three indentations 18. As may be noted from the partial column view of FIG. 4, indentation 18 provides a small passage between sphere 14 and valve seat 19 such that liquids in the chamber 17 above the valve can drain through the passage as indicated by arrows A and drops 21. When sphere 14 is closed in its valve seat 19, condensation of the heavier fractions in the chamber above ball valve 12 of FIG. 4 will not flood chamber 17 as in the prior art since the passages formed by indentations 18 will permit drainage and therefore the ball surface is free of any tendency to stick in the valve seat orifice.

As will be recognized, when the column shown partially in FIG. 4 is in operation, the rising vapors will lift ball valve 12 off of seat 19 permitting the vapors to rise through the column into chamber 17. The heavier fractions, which may condense in chamber 17 and those above, will drain through the open valve formed by seat 19 and ball valve 12 toward the lower end of column 10. Indentations 18 are effective to cause rotation and continual movement of ball valve 12 from the rising vapors which will tend to prevent buildup of condensed compounds and the like on the valve seat and any tendency for the ball to stick in its seat. This feature also assures optimum vapor/liquid contact for effective separation of the vapor and liquid.

It has been found that an alternative shape for the floating ball vapor valve is advantageous for microcolumns. FIG. 5 and FIG. 6 show the preferred mushroom design for floating ball vapor valve 20 for use in a microcolumn. The ball portion 22 is somewhat hemispherical with the area forming the valve seat curved in a so-called mushroom shape. Indentations 26 are made in the area which will form the valve seat when valve 20 is installed in its column. The horizontal undersurface of the ball portion 22 of valve 20 provides a greater lifting surface to the rising vapors in small columns than in the spherical shape valves. Otherwise, the operation and effectiveness of the ball valve 20 is the same as ball valve 12 preferred for a standard Snyder column.

It will be obvious to those of skill in the art that the ball valve of the invention can be modified in shape to suit particular applications and may have cone shapes, hemispherical shapes and others as long as the required indentations are provided. These novel valves, as will be obvious, may be used in other types of distillations than disclosed. Thus, such changes and modifications are to be considered within the spirit and scope of the invention.

I claim:

1. Apparatus for separation of volatiles from heavier fractions comprising:
   a vertically oriented distillation column having a plurality of chambers, adjacent ones of said chambers separated by orifices forming valve seats; and
   a plurality of floating ball vapor valves, each of said valves having a hollow ball portion, a lower surface of said ball portion forming a valve face, said valve face having indentations therein, said ball portion having a downwardly extending stem portion wherein one of said valves is disposed in each of said orifices with said valve face in contact with said valve seat and said indentations forming liquid flow passages between adjacent ones of said chambers;
   whereby said indentations serve to prevent flooding of said chambers.

2. Apparatus for separation of volatiles from heavier fractions comprising:
   a vertically oriented cylindrical glass distillation column;
   a plurality of circular indentations concentric with said column thereby dividing said column into a plurality of chambers;
   a valve seat formed by the interior part of said circular indentations; and
   a hollow glass ball type lift valve disposed in each of said valve seats, said valve including an upper ball portion and a lower stem portion extending downwardly through said valve seat, said valve having multiple indentations in the surface thereof in contact with said valve seat;
   whereby said valves are lifted by rising vapors and rotated thereby to prevent sticking and flooding.

3. In a glass floating ball vapor valve for distilling columns and the like, the improvement comprising:
a hollow ball portion having a valve face surface, said surface having multiple indentations therein, said indentations forming valve by-pass passages for preventing flooding of said column; and
a downwardly extending guide portion.

4. The apparatus as defined in claim 1, 2 or 3 in which said ball portion of said valves is spherical.

5. The apparatus as defined in claim 1, 2 or 3 in which said ball portion of said valves is mushroom shaped.

* * * * *